US006860875B2

(12) United States Patent
Hsue et al.

(10) Patent No.: US 6,860,875 B2
(45) Date of Patent: Mar. 1, 2005

(54) METHOD AND APPARATUSES OF USING FORAMEN CATHETER NEEDLE SCOPE TO INDUCE TEMPORARY BLOCKADE OF SACRAL NERVES

(75) Inventors: Chaosong Hsue, P.O. Box 2103, Taichung (TW); Yung Kuei Soong, P.O. Box 2103, Taichung (TW); Esther Shih-Chu Ho, P.O. Box 2103, Taichung (TW); Wu-Chou Lin, P.O. Box 2103, Taichung (TW)

(73) Assignees: Chaosong Hsue, Taichung (TW); Yung Kuei Soong, Taichung (TW); Esther Shih-Chu Ho, Taichung (TW); Wu-Chou Lin, Taichung (TW); Hung Hui Chen, Taichung (TW)

( * ) Notice: Subject to any disclaimer, the term of this patent is extended or adjusted under 35 U.S.C. 154(b) by 137 days.

(21) Appl. No.: 10/302,911

(22) Filed: Nov. 25, 2002

(65) Prior Publication Data
US 2004/0102760 A1 May 27, 2004

(51) Int. Cl.⁷ ............................................. A61M 31/00
(52) U.S. Cl. ...................................................... 604/512
(58) Field of Search .................................. 604/500, 506, 604/508–512, 515, 264, 164.01; 600/101, 103, 114, 160; 606/108

(56) References Cited

U.S. PATENT DOCUMENTS 6,251,115 B1 * 6/2001 Williams et al. ............ 606/108

* cited by examiner

Primary Examiner—Michael J. Hayes
(74) Attorney, Agent, or Firm—Rosenberg, Klein & Lee

(57) ABSTRACT

A using method and apparatuses of foramen catheter needle scope of the present invention uses a new approach, new sites and set of apparatuses to block sacral nerves or nerve plexus to reduce pain during operating. The present invention uses an endoscopic video system with foramen catheter needle scope to introduce anesthetic agents via catheter through foramen of sacral bone to block the sympathetic and parasympathetic nerve fibers of lower pelvis, which includes the innervation of uterus, vaginal canal and perineum.

1 Claim, 13 Drawing Sheets

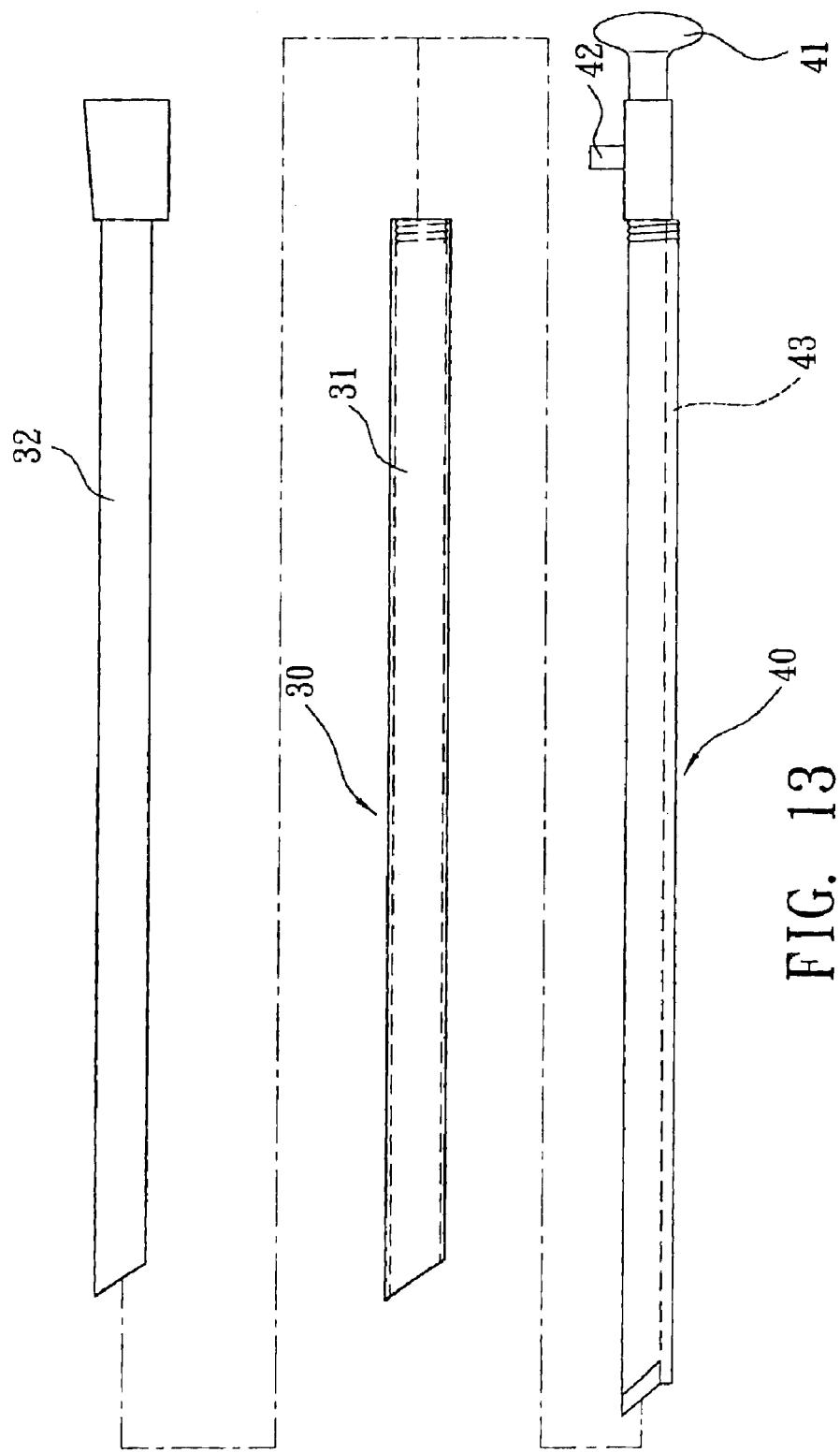

METHOD AND APPARATUSES OF USING FORAMEN CATHETER NEEDLE SCOPE TO INDUCE TEMPORARY BLOCKADE OF SACRAL NERVES

BACKGROUND OF THE INVENTION

1. Field of the Invention

The present invention relates to a method and apparatuses of using foramen catheter needle scope, and more particularly to a method and apparatuses of using foramen catheter needle scope to induce temporary blockade of sacral nerves.

The present invention pertains to an endoscopic video system attached to a foramen catheter needle scope, a catheter being introduced to the foramen of sacrum and administration of anesthetic agents via catheter through foramen of sacrum to block the sympathetic and parasympathetic nerve fibers of lower pelvis include sympathetic trunk, sympathetic ganglion, fibers of S2, S3, S4, parasympathetic or Nervi Erigentes, inferior hypo gastric nerve plexus, pelvic plexus and utero sacral nerve plexus, pudendal nerve and perineal nerve.

2. Description of Related Art

Conventional methods of painless or reduce pain techniques used in labor course include the following examples. Inhalation anesthesia is inhalation of evaporative gaseous product to induce systemic general anesthesia, which is considering dangerous to mother and body. Epidural anesthesia, is to introduce nerve blocking agents into epidural space, also has the disadvantages of immobilization when onset and dangerous of spinal shock to mother and body. Caudal block, pudendal block and local anesthesia can block pain while third stage and delivery of fetal head, few effect at first and second stage of uterine contraction pain. Paracervical block is to inject anesthetic agents along cervix to block the innervation of lower segment of uterus, usually failure to block the upper portion pain when uterine contract, and often dislodged of catheter when progress of labor or effacement of cervix changes.

Consequently, a safer technique to help women reduce pain or induce painless is always welcomed and to be improved upon.

SUMMARY OF THE INVENTION

The main objective of the present invention is to provide a solution to the problem described above.

To achieve the objective, using endoscopic video system, trocar, foramen needle scope with operation openings, catheter, fixation tapes and injection agents and devices, which entails the following procedure:

1. The patient is placed in a lateral recumbent, sitting, prone or semi prone flexed position.
2. Disinfect of the operation field.
3. Local anesthesia administrated to the sacral area.
4. Introducing foramen catheter needle scope follow trocar applied then attach to video system to locate foramen of sacrum of one side.
5. Check and treat bleeding point.
6. Introducing of catheter from the scope through foramen of sacrum to the area covers sympathetic trunk, sympathetic ganglion, sacral S2, S3, S4, parasympathetic or Nervi Erigentes, inferior hypogastric nerve plexus, pelvic nerve plexus and utero sacral nerve plexus.
7. Anesthetic agents administrated to block the afferent and efferent neurons of the innervation of sympathetic trunk, sympathetic ganglion, sacral nerve S2, S3, S4, parasympathetic or Nervi Erigentes, inferior hypogastric plexus and utero sacral plexus.
8. Tape the catheter tightly to the skin after remove of foramen catheter needle scope and trocar.
9. Repeat steps of 4, 5, 6, 7 and 8 of the other side foramen of sacrum.
10. Administration of anesthetic agents through catheters per needed.
11. Remove catheters to conclude the procedure.

Further benefits and advantages of the present invention will become apparent after a careful reading of the detailed description with appropriate reference to the accompanying drawings.

BRIEF DESCRIPTION OF THE DRAWINGS

FIG. 13 is a side exploded plan view of another embodiment of a foramen catheter needle scope in accordance with the present invention.

DETAILED DESCRIPTION OF THE INVENTION

Figure 1:
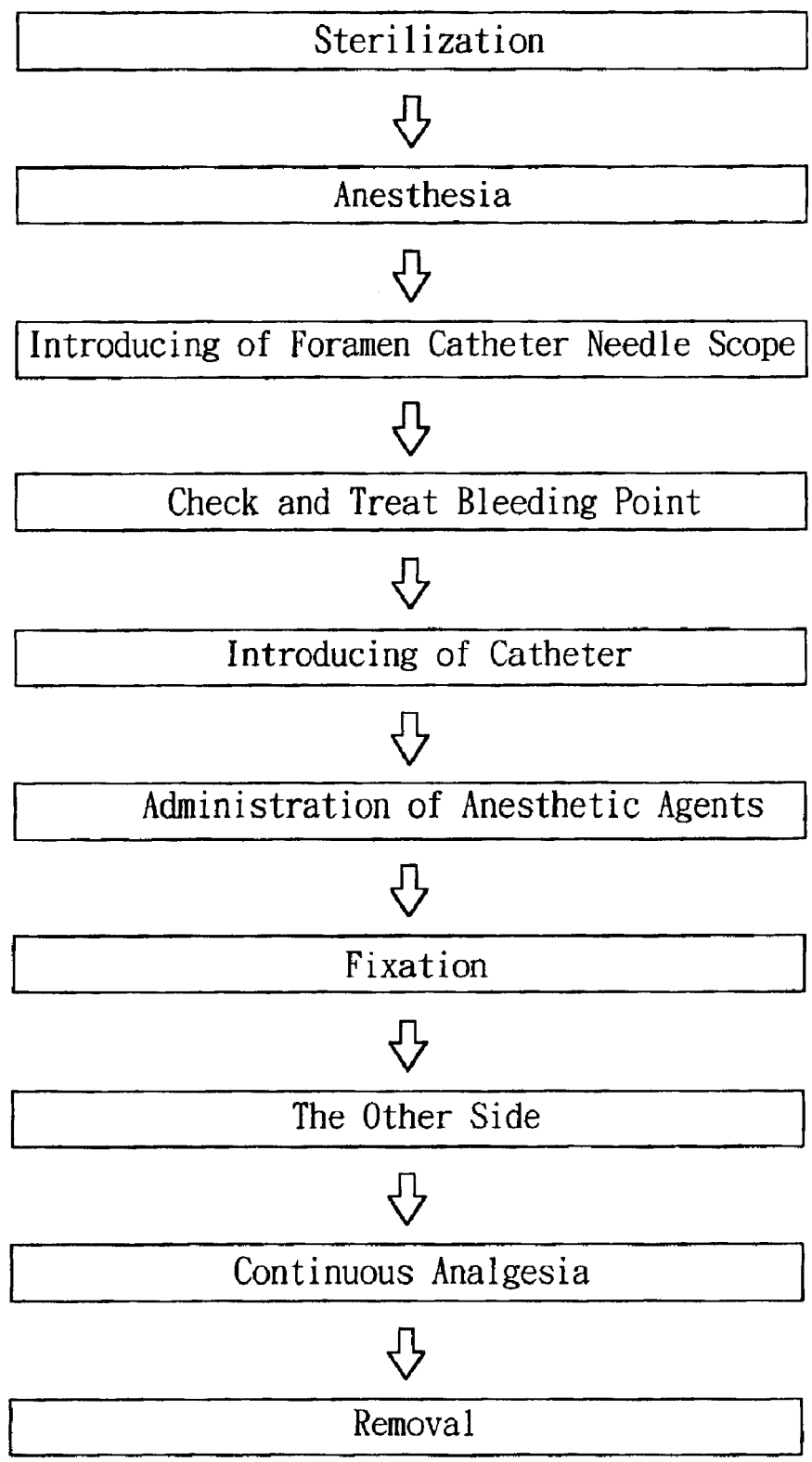
FIG. 1 is a flow chart of a method of using foramen catheter needle scope of the present invention to induce temporary blockade of sacral nerves.
Figure 2:
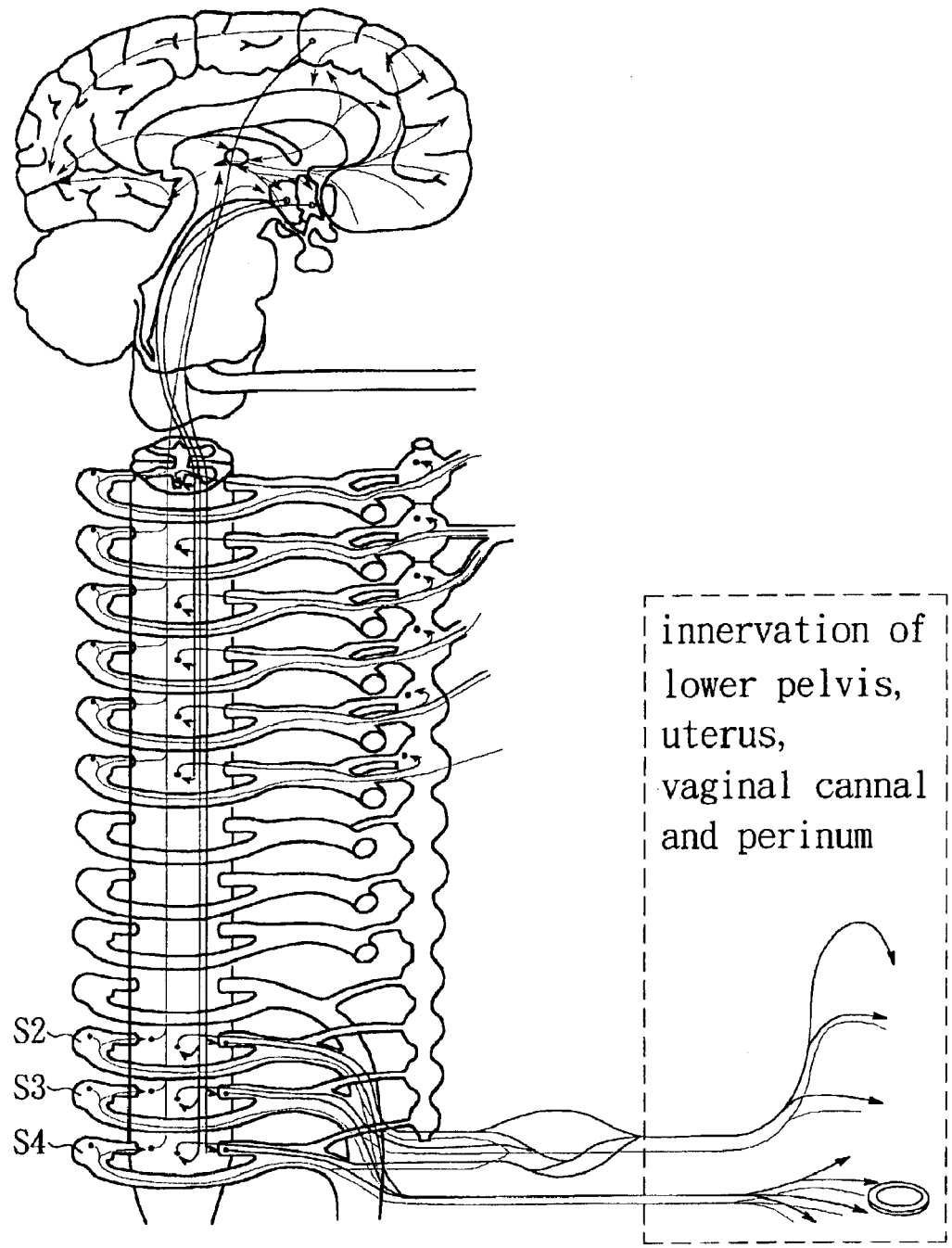
FIG. 2 is a partial side plan view of the nerve system of sacral area.
Figure 3:
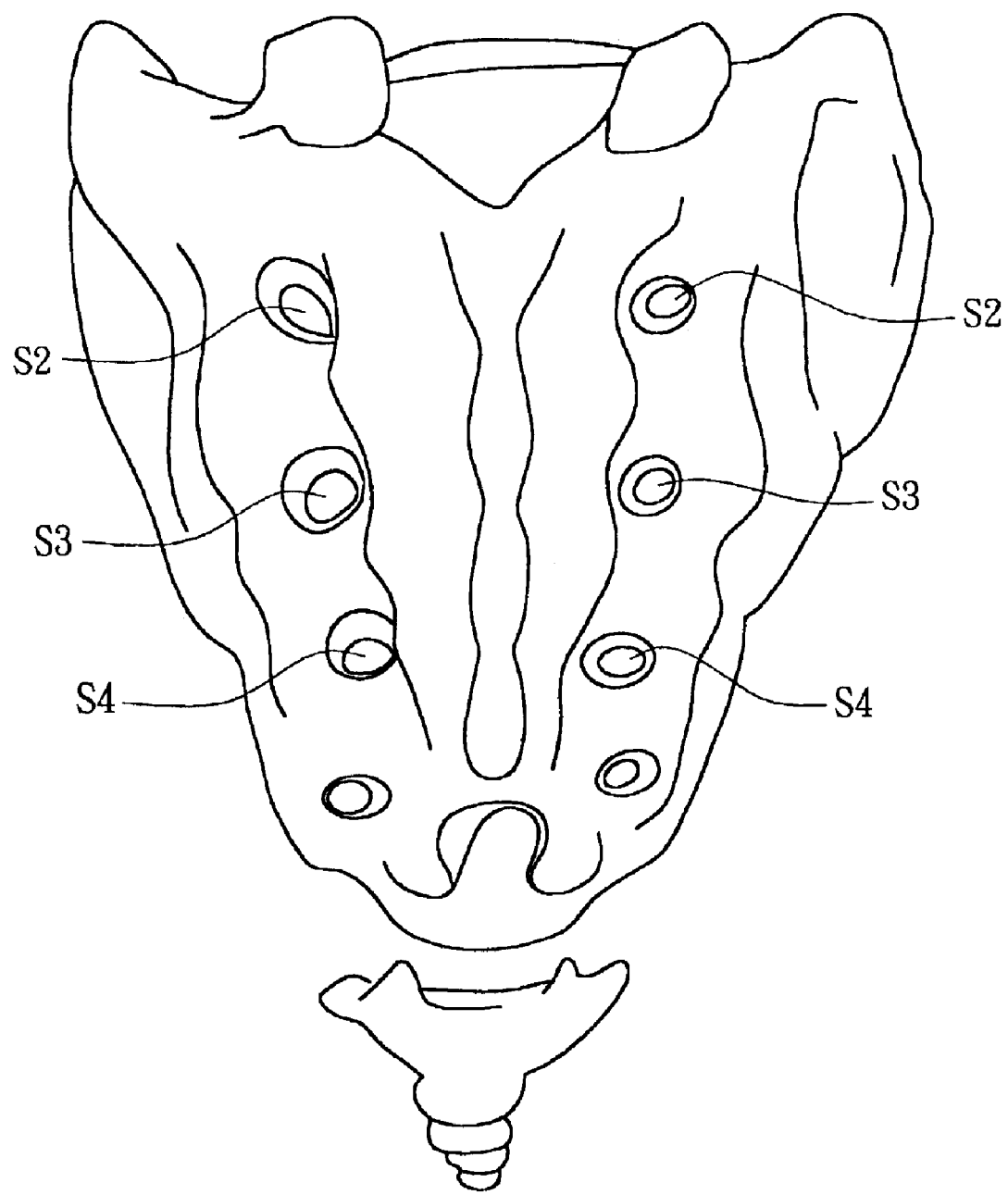
FIG. 3 is a rear plan view of the sacrum and coccyx.
Figure 4:
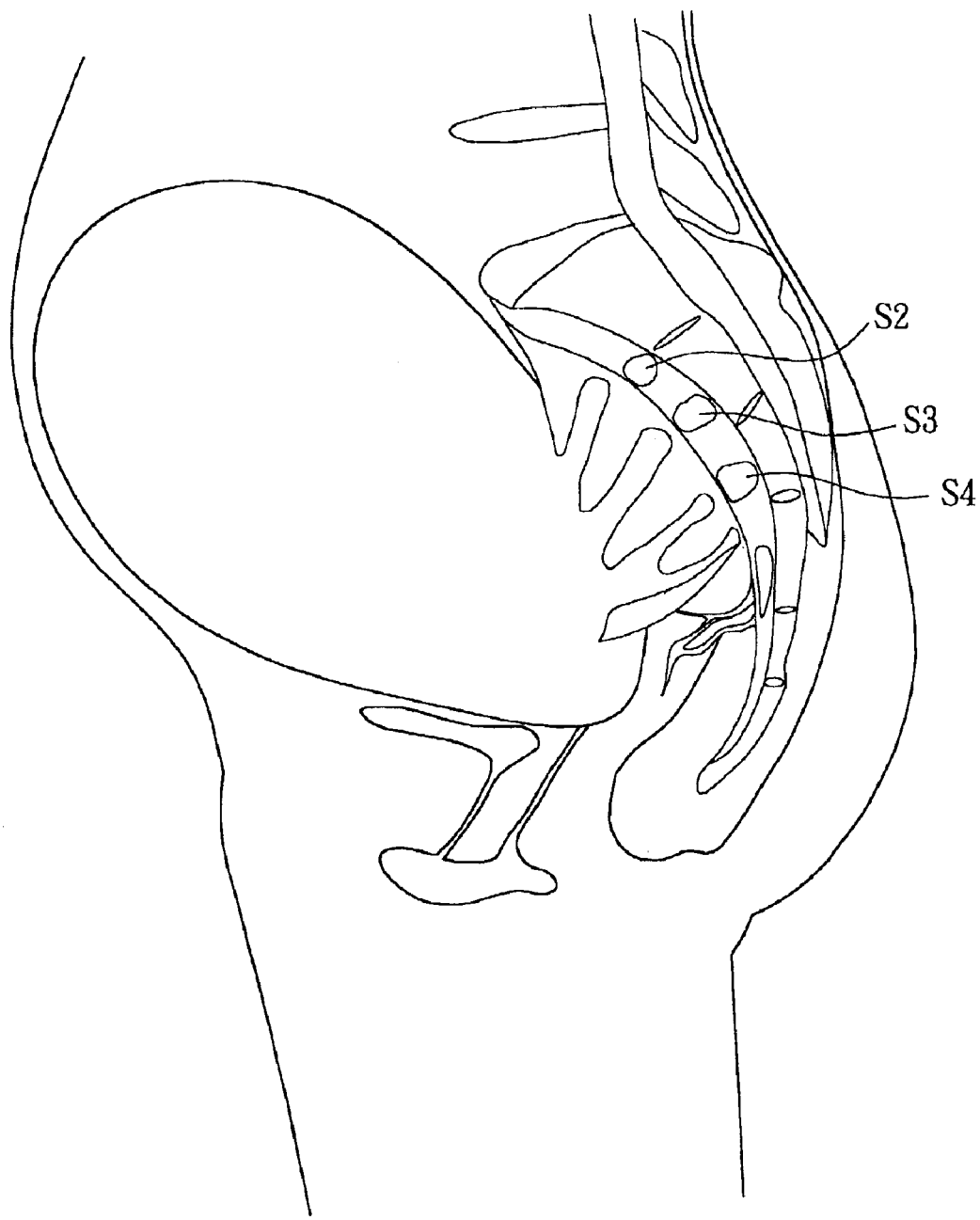
FIG. 4 is a side plan view of lower pelvis of sacral area.
Figure 5:
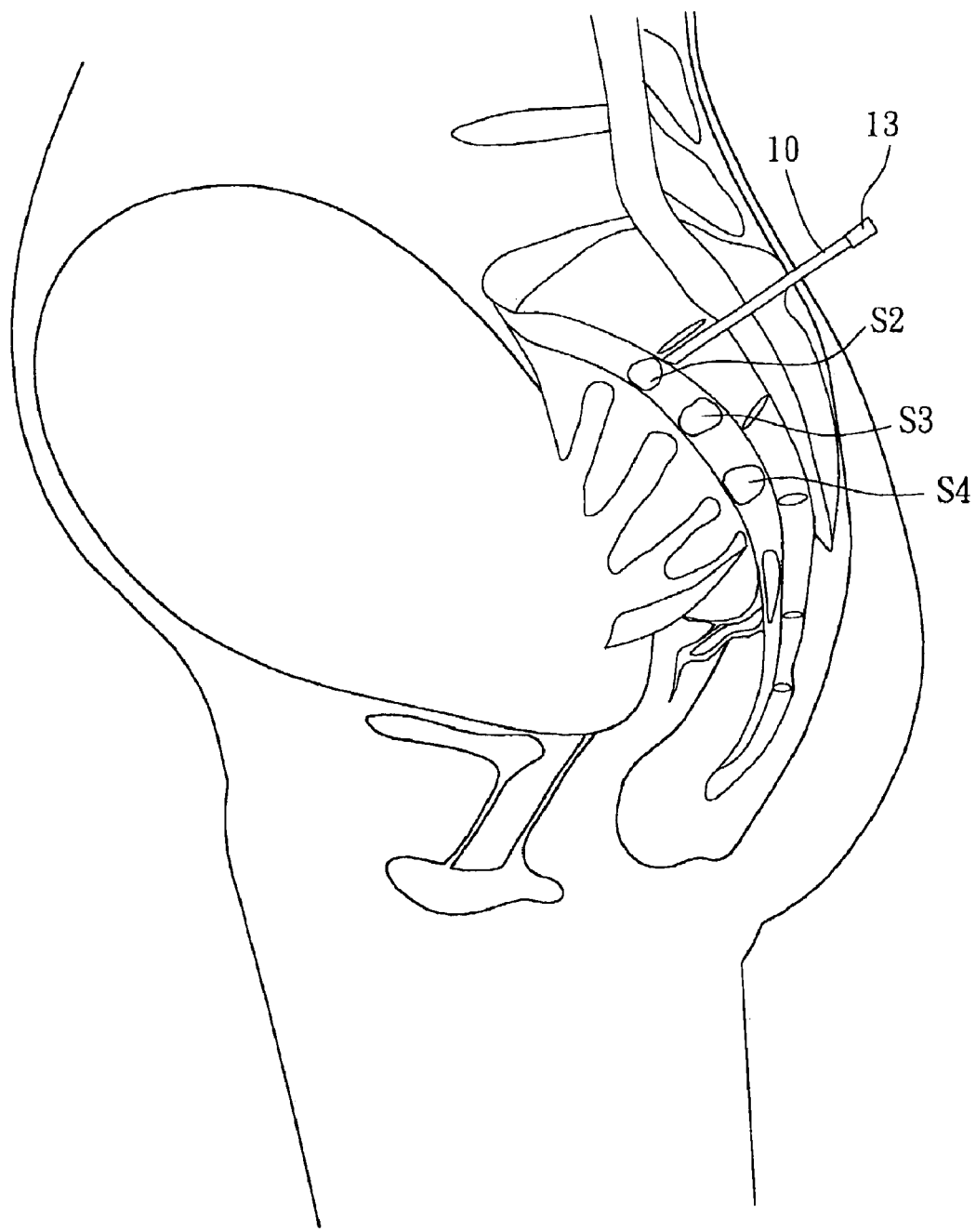
FIG. 5 is a side operational view of the method of the present invention in FIG. 1.
Figure 6:
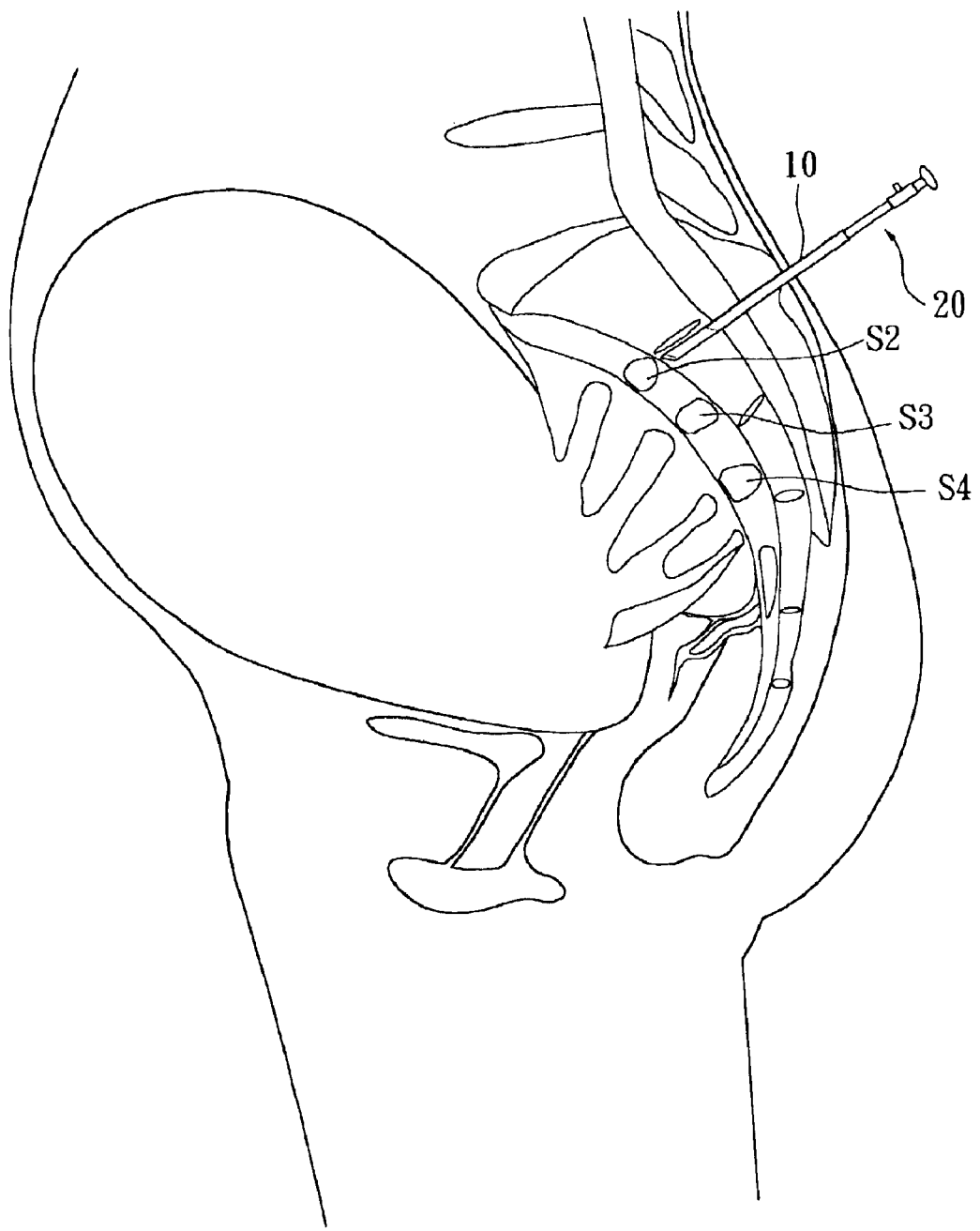
FIG. 6 is a side operational view of the method of the present invention in FIG. 1.
Figure 7:
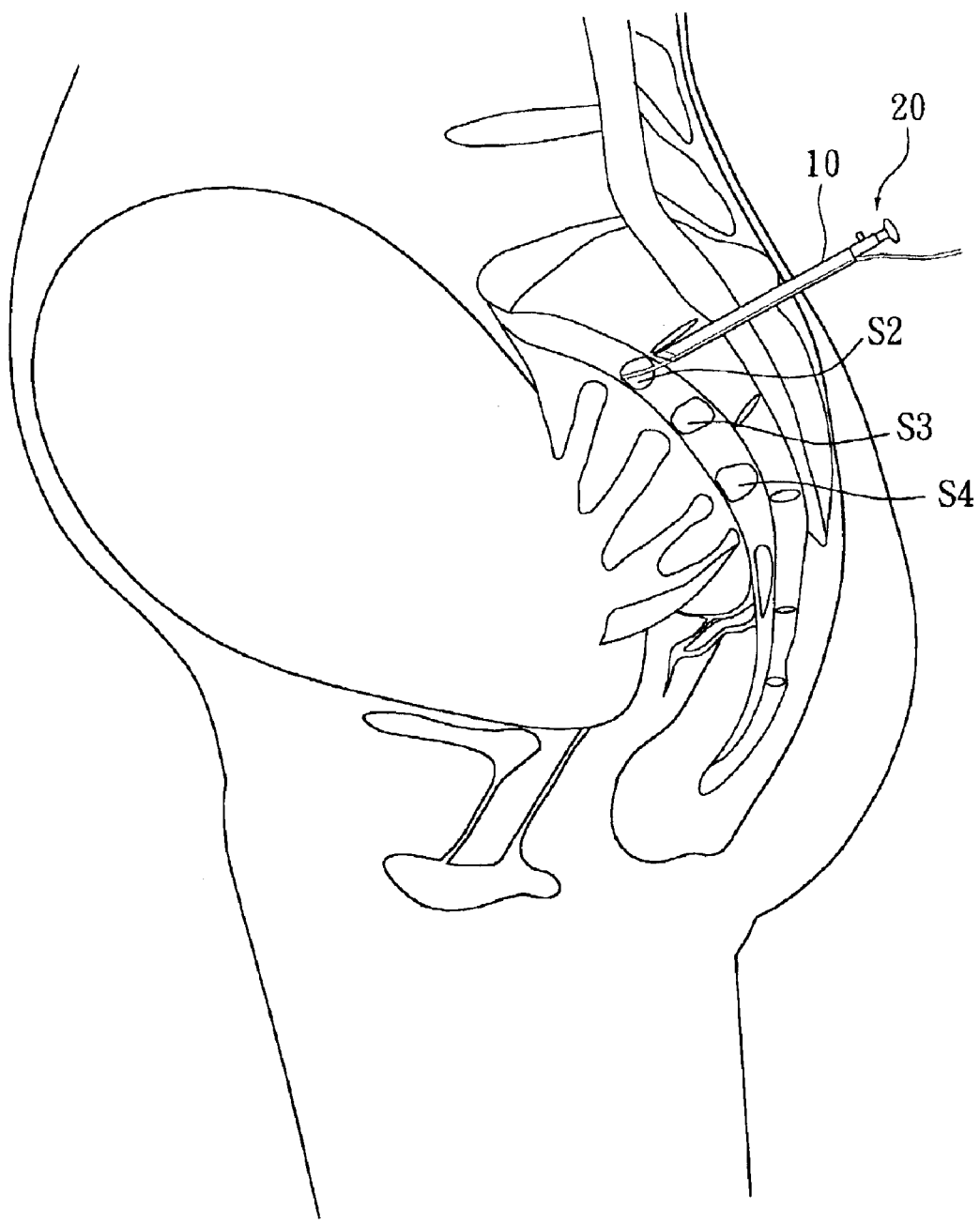
FIG. 7 is a side operational view of the method of the present invention in FIG. 1.
Figure 8:
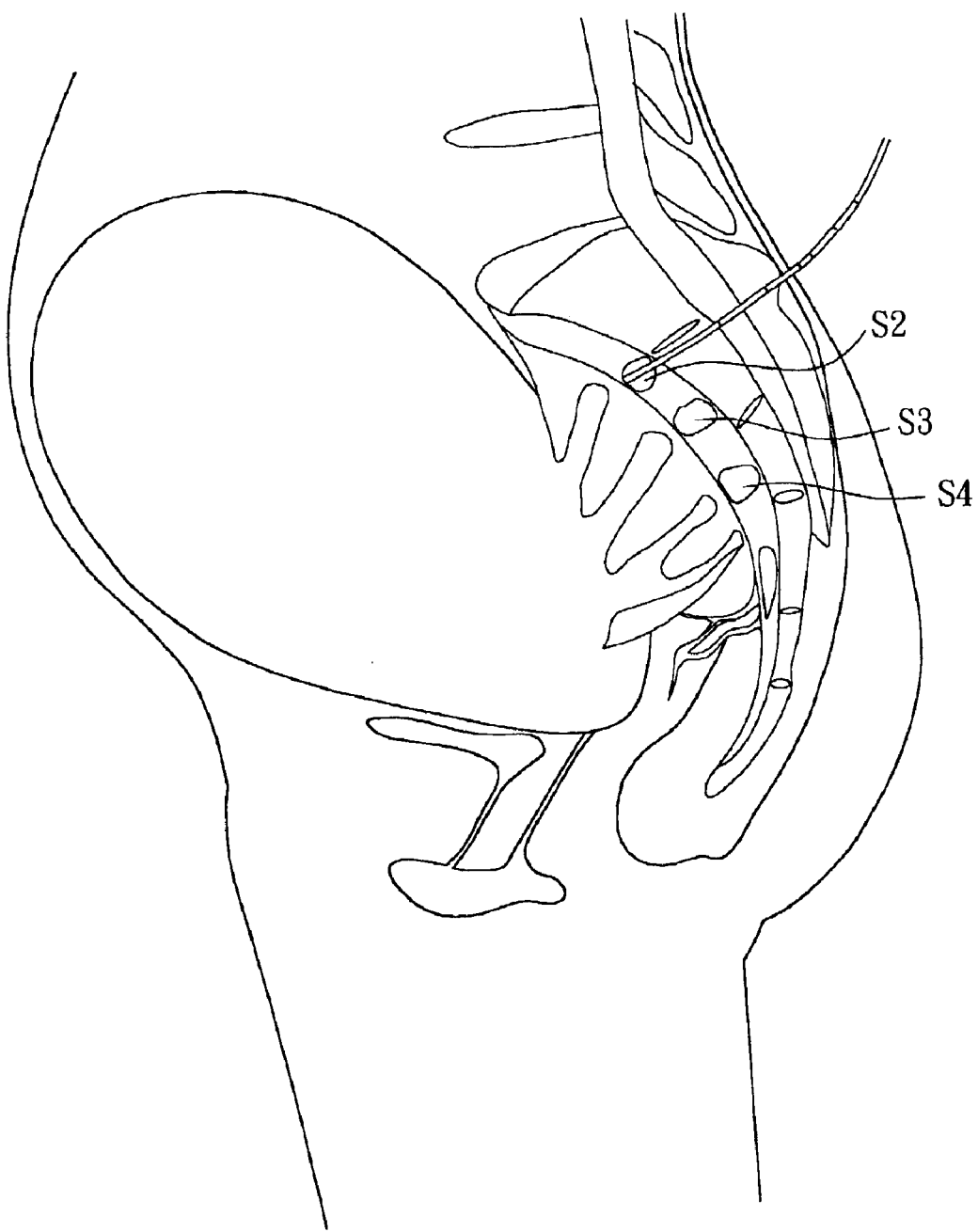
FIG. 8 is a side operational view of the method of the present invention in FIG. 1.
Figure 9:
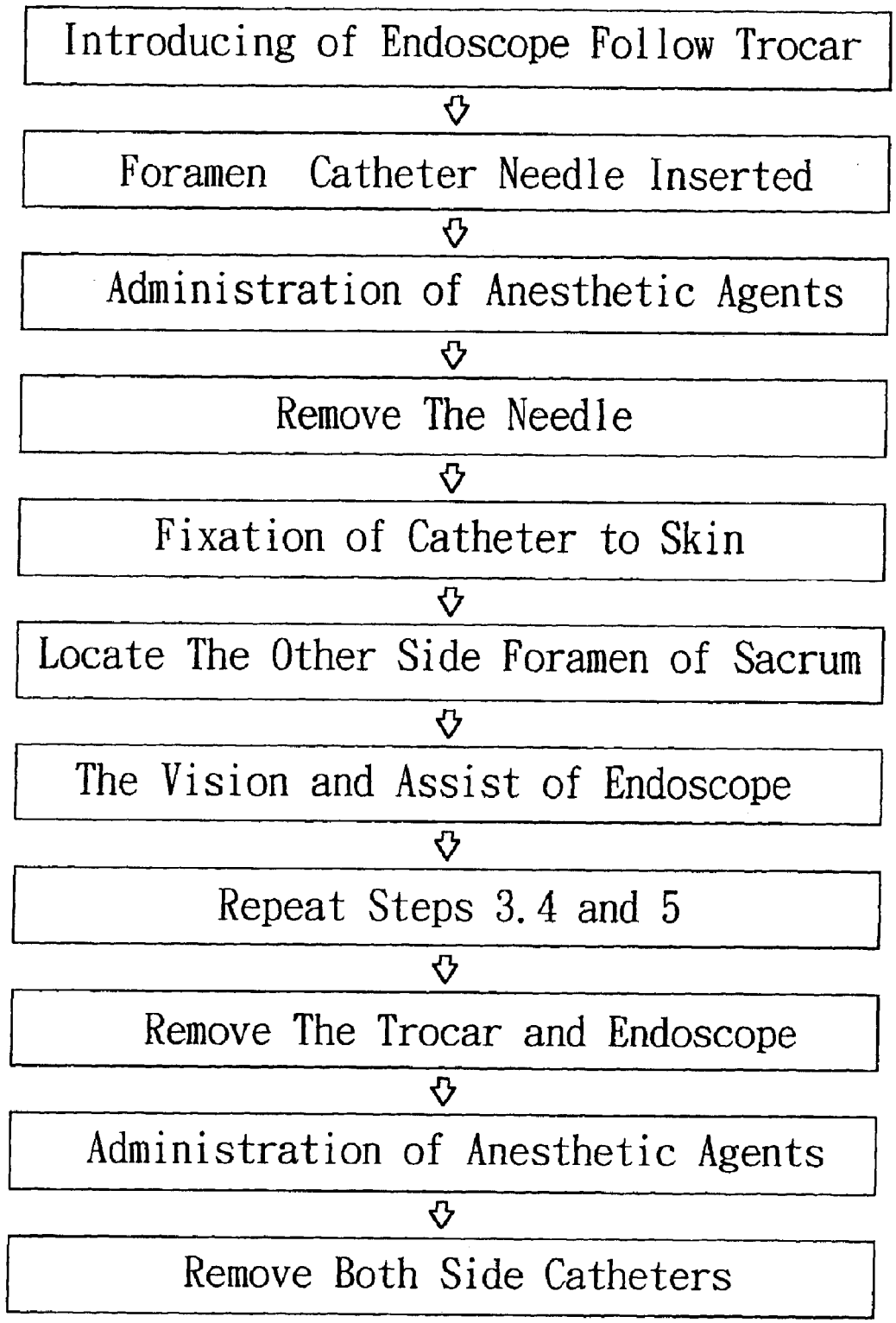
FIG. 9 is a flow chart of another method of using foramen catheter needle scope of the present invention to induce temporary blockade of sacral nerves.

Referring to the drawings and initially to FIGS. 1–8 and 11–12, a method and apparatuses of using foramen catheter needle scope to induce a temporary blockade of sacral nerves in accordance with the present invention comprises following procedures.

Step A—Sterilization: The patient is placed in lateral recumbent, sitting, prone or semi prone flexed position, disinfect of the operation filed properly.

Step B—Anesthesia: Local anesthesia is given to sacral area.

Step C—Introducing of foramen catheter needle scope: Introducing foramen catheter needle scope follow trocar applied then attach to video system to locate foramen of sacrum of one side.

Step D—Check and treat bleeding point.

Step E—Introducing of catheter: Introducing of catheter within the scope through foramen of sacrum to the area covers sympathetic trunk, sympathetic ganglion, sacral nerve S2, S3, S4, parasympathetic or Nervi Erigentes, inferior hypogastric nerve plexus, pelvic nerve plexus and utero sacral nerve plexus.

Step F—Administration of anesthetic agents: Anesthetic agents administrated to block the afferent and efferent neurons of the innervation of sympathetic trunk, sympathetic ganglion, sacral nerve S2, S3, S4, parasympathetic or Nervi Erigentes, inferior hypogastric plexus, pelvic plexus and utero sacral plexus.

Step G—Fixation: Tape the catheter tightly to the skin after remove of foramen catheter needle scope and trocar.

Step H—The other side: Repeat steps C, D, E, F and G of the other side foramen of sacrum.

Step I—Continuous analgesia: Administration of anesthetic agents through catheters per needed.

Step J—Removal: Remove catheters to conclude the procedure.

This technique is safe and effective to provide a new version to reduce pain or induce painless during labor course.

Using method and apparatus of foramen catheter needle scope to induce temporary blockade of sacral nerves and reduce pain is a method using endoscopic video system, trocar and foramen catheter needle scope to introduce a catheter through foramen of sacrum to area covers nerve fibers of sympathetic trunk, sympathetic ganglion, sacral nerves S2, S3, S4, pelvic splanchnic nerves (Nervi Erigentes), inferior hypogastric plexus, pelvic plexus, utero sacral plexus, pudendal nerve and perineal nerve, then anesthetic agents can be administrated to both side of the area via catheters continuously per needed to reduce pain or induce painless of lower pelvis. The catheters are tightly attached to the skin with adhesive tapes to avoid dislodgement. Catheters are removed to conclude the procedure after operation.

Furthermore, with reference to FIGS. 2–3 and 9–11, a modification of using endoscopic assist foramen catheter needle to induce temporary blockade sacral nerves includes the using of following method and apparatus.

1. Introducing of endoscope follow trocar applied at sacral area.
2. A foramen catheter needle is inserted to introduce catheter from the needle to one side foramen of sacrum under the vision and assist of endoscope.
3. Administration of anesthetic agents through foramen of sacrum via catheter.
4. Remove the needle.
5. Fixation of catheter to skin.
6. Using endoscope to locate the other side foramen of sacrum.
7. A foramen catheter needle is inserted to introduce catheter from the needle to the other side foramen of sacrum under the vision and assist of endoscope.
8. Repeat step 3, 4 and 5.
9. Remove the trocar and endoscope.
10. Administration of anesthetic agents through each side foramen of sacrum via catheter per needed.
11. Remove both side catheters after birth to conclude the procedure.

Figure 12:
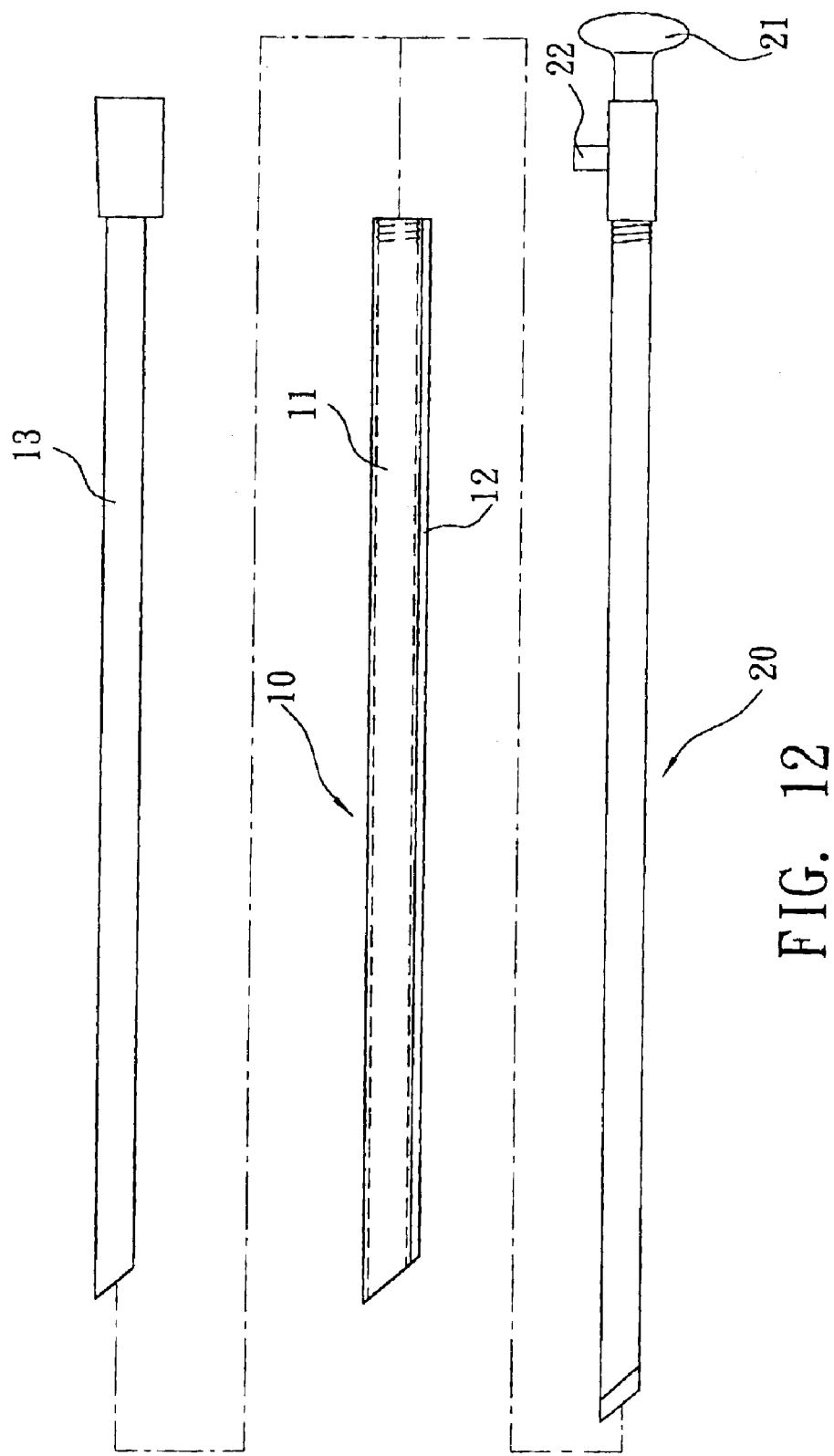
FIG. 12 is a side exploded plan view of a foramen catheter needle scope in accordance with the present invention.

With reference to FIG. 12, the foramen catheter needle scope as described above comprises an outer sheath (10) including a first passage (11) longitudinally defined in the outer sheath (10) and extending through the outer sheath (10), and a second passage (12) longitudinally defined in the outer sheath (10) and extending through the outer sheath (10). A stick-like plug (13) is previously fully received in the first passage (11). The first passage (11) is provided to partially receive a foramen catheter needle scope (20) after the outer sheath (10) with the plug (13) being inserted into the sacral area and the plug (13) being removed from the outer sheath (10). The second passage (12) is defined for partially receiving a catheter (not shown) to inject anesthetic agents to the area cover sacrum nerves. The foramen catheter needle scope (20) has an optic device (21) mounted thereon and a connector/adaptor (22) provided to be connected to a cold light source (not shown) and a digitally controlled video system (not shown).

With reference to FIG. 13, it is another embodiment of the foramen catheter needle scope of the present invention. The foramen catheter needle scope comprises an outer sheath (30) including a passage (31) longitudinally defined in the outer sheath (30) and extending through the outer sheath (30), and a stick-like plug (32) previously received in the passage (31) in the outer sheath (30). A foramen catheter needle scope (40) is partially received in the passage (31) in the outer sheath (30) after the outer sheath (30) with the plug (32) being inserted into the sacral area and the stick-like plug (32) removed from the outer sheath (30). The foramen catheter needle scope (40) includes an optic device (41) mounted thereon, a connector/adaptor (42) formed to be connected to a cold light source (not shown) and a digitally controlled video system (not shown), and a passage (43) longitudinally defined in the foramen catheter needle scope (40) and extending along the foramen catheter needle scope (40) for receiving a catheter to inject anesthetic agents to the sacral nerves.

Figure 10:
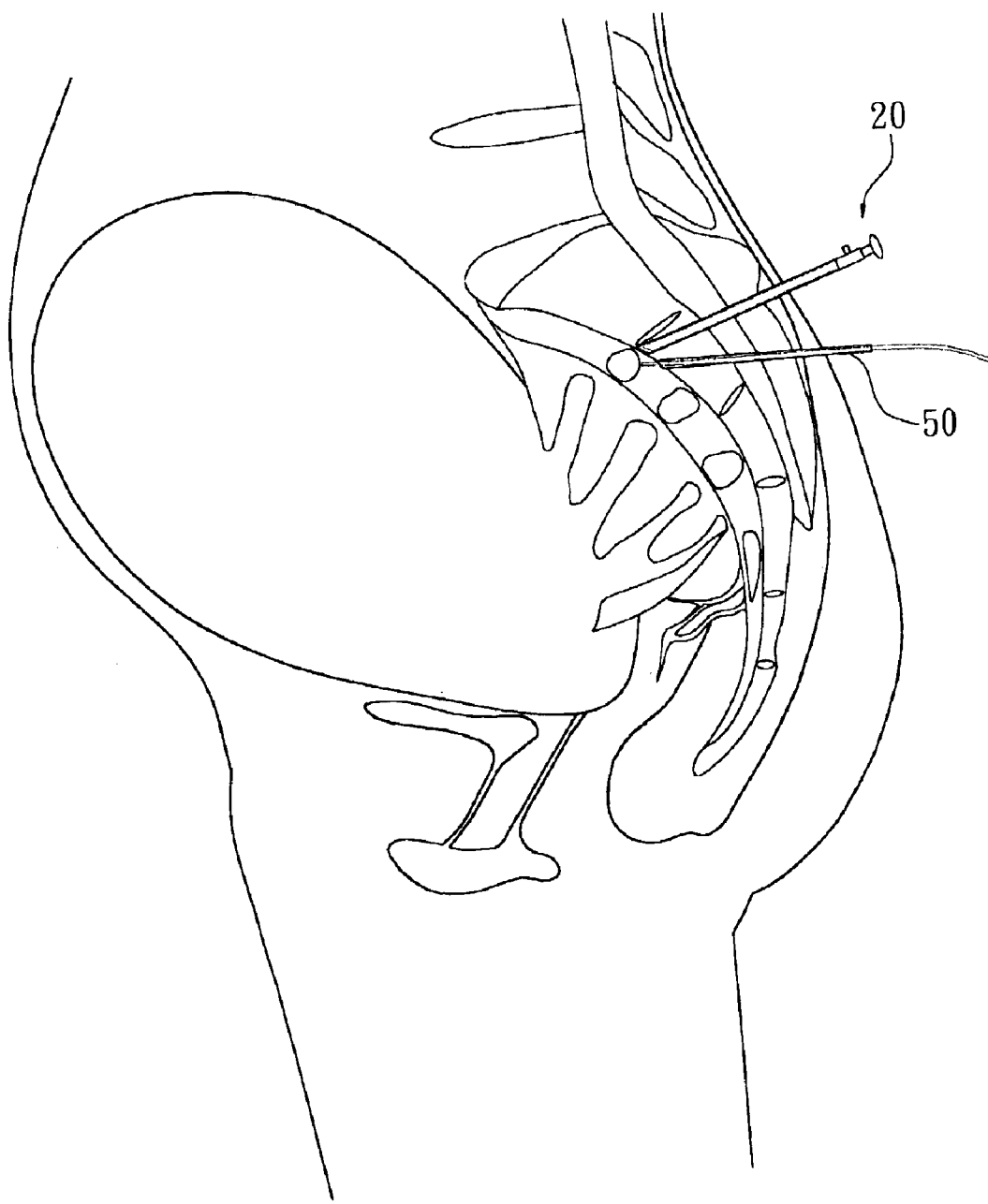
FIG. 10 is a side operation view of the method of the present invention in FIG. 9.
Figure 11:
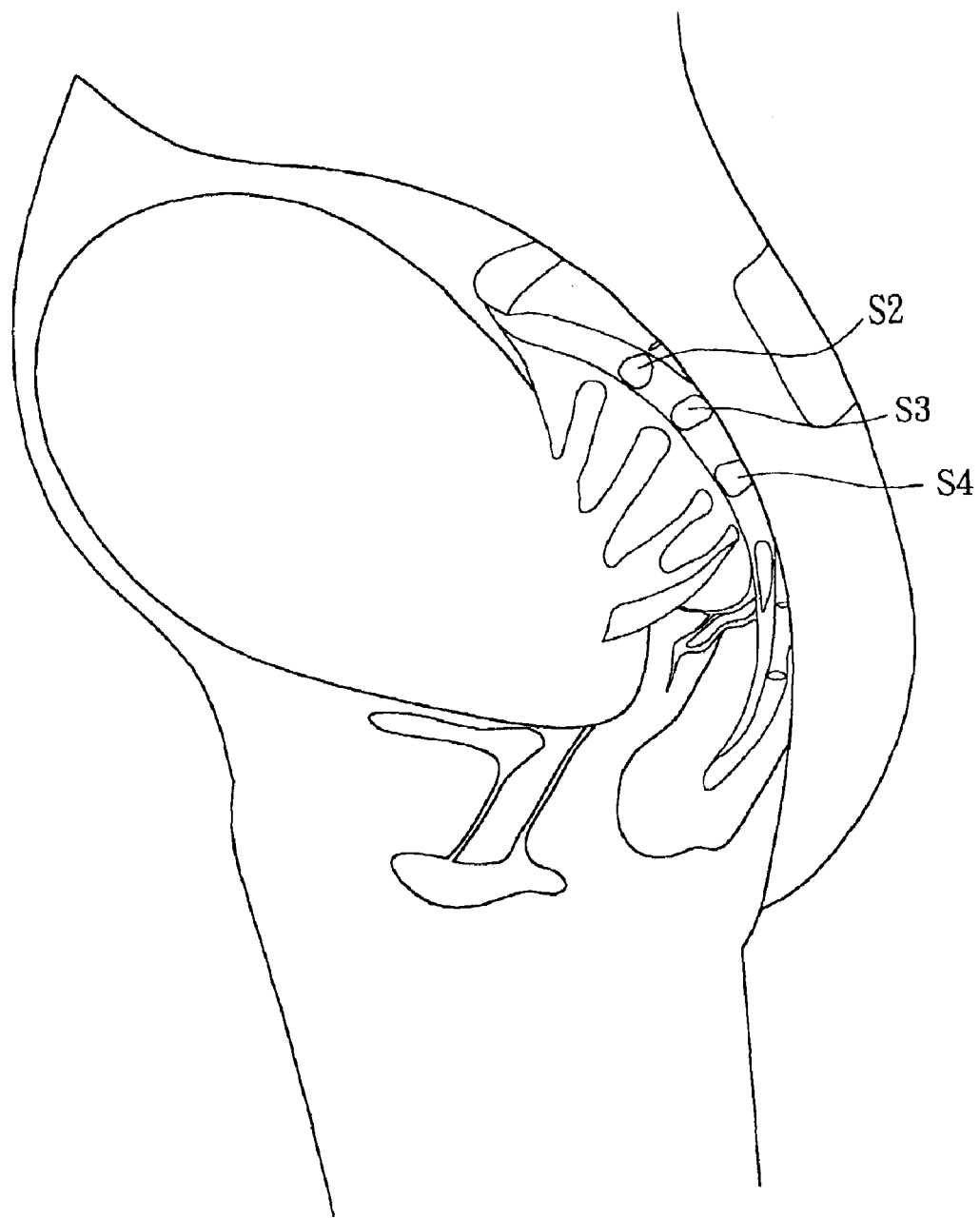
FIG. 11 is a side operational view of the method of the present invention in FIG. 9.

Furthermore, with reference to FIGS. 10 and 11 that show another method to use the present invention. An endoscope has been introduced close to middle of sacral area to locate both sides foramen of sacrum. A foramen catheter needle is introduced at the second puncture site of sacral area close to one side foramen of sacral bone. Under the vision and assist of endoscope, the tip of foramen catheter needle (50) and foramen of sacrum can be easily identified. The foramen catheter in the needle then is introduced through foramen of sacrum to the area that covers the innervation of sacral nerves S2, S3 and S4, and anesthetic agents then is administrated to block the innervation of the area. A third puncture site is made to the other side of sacral area close to the other side foramen of sacrum. Then make the same to block the innervation covers the other side sacral nerves.

Although the invention has been explained in relation to its preferred embodiment, it is to be understood that many other possible modifications and variations can be made without departing from the spirit and scope of the invention as hereinafter claimed.

What is claimed is:

1. A method of using foramen catheter needle scope to induce a temporary blockade of sacral nerves and to reduce pain, comprising the steps of:

Step A—Sterilization: The patient is placed in lateral recumbent, sitting, prone or semi prone flexed position, disinfect of the operation filed properly;

Step B—Anesthesia: Local anesthesia is given to sacral area;

Step C—Introducing of foramen catheter needle scope: Introducing foramen catheter needle scope follow trocar applied then attach to video system to locate foramen of sacrum of one side;

Step D—Check and treat bleeding point;

Step E—Introducing of catheter: Introducing of catheter within the scope through foramen of sacrum to the area covers sympathetic trunk, sympathetic ganglion, sacral nerve S2, S3, S4, parasympathetic or Nervi Erigentes, inferior hypogastric nerve plexus, pelvic nerve plexus and utero sacral nerve plexus;

Step F—Administration of anesthetic agents: Anesthetic agents administered to block the afferent and efferent neurons of the innervation of sympathetic trunk, sympathetic ganglion, sacral nerve S2, S3, S4, parasympathetic or Nervi Erigentes, inferior hypogastric plexus, pelvic plexus and utero sacral plexus;

Step G—Fixation: Tape the catheter tightly to the skin after remove of foramen catheter needle scope and trocar;

Step H—The other side: Repeat steps C, D, E, F, and G of the other side of foramen of sacrum;

Step I—Continuous analgesia: Administration of anesthetic agents through catheters per needed; and Step J—Removal: Remove catheters to conclude the procedure after operation.

* * * * *